United States Patent [19]

Egan et al.

[11] 4,097,751
[45] Jun. 27, 1978

[54] RETROREFLECTANCE MEASURING APPARATUS

[75] Inventors: Walter G. Egan, Woodhaven; Herbert B. Hallock, Huntington; Theodore W. Hilgeman, Deer Park, all of N.Y.

[73] Assignee: Grumman Aerospace Corporation, Bethpage, N.Y.

[21] Appl. No.: 726,262

[22] Filed: Sep. 24, 1976

[51] Int. Cl.² ............................................. G01N 21/30
[52] U.S. Cl. .................................. 250/571; 356/211
[58] Field of Search ............... 250/571, 262, 272, 200, 250/572; 356/120, 211, 209

[56] References Cited

U.S. PATENT DOCUMENTS

| | | | |
|---|---|---|---|
| 3,606,541 | 9/1971 | Sugano et al. | 356/120 |
| 3,804,532 | 4/1974 | Patten et al. | 356/211 X |
| 3,836,787 | 9/1974 | Ash | 250/572 |
| 3,892,494 | 7/1975 | Baker et al. | 356/120 |
| 3,904,293 | 9/1975 | Gee | 356/120 X |
| 3,977,789 | 8/1976 | Hunter et al. | 356/120 |

*Primary Examiner*—David C. Nelms
*Assistant Examiner*—Vincent J. Sunderdick
*Attorney, Agent, or Firm*—Mellor A. Gill

[57] ABSTRACT

An instrument for measuring the retroreflectance properties of surfaces to angles including an angle of zero degrees of the incident beam. The instrument comprises a source of collimated radiation, a beam splitter such as a cube biprism, a beam chopper, a radiation sensor system operated in a coherent detection mode with the chopper, and indicating and/or recording means. A beam of radiation aimed at a normal incidence at the surface of the test specimen is passed through the biprism which has its 45° diagonal semi-reflecting surface interposed in the beam. The undesirable part of the beam is reflected off the diagonal surface to and through one of the sides of the biprism and the reflection back therefrom passes through the diagonal surface and then travels to the radiation sensor. The desirable part of the beam from the radiation source goes directly through the diagonal surface and passes to the surface of the specimen. Radiation incident on the specimen surface is reflected back to the biprism whence it is partially reflected off the diagonal surface and it too passes to the sensor. The chopper is interposed in the radiation path between the biprism and the specimen and periodically interrupts the radiation therebetween. The sensor is operated in a coherent-detection background-discrimination mode with the chopper such that a signal indicating the retroreflectance properties of the specimen surface is obtained.

1 Claim, 3 Drawing Figures

RETROREFLECTANCE PROPERTIES OF $BaSO_4$ AT $\lambda\mu m = 0.600$
NORMAL INCIDENCE

RETROREFLECTANCE MEASURING APPARATUS

BACKGROUND OF THE INVENTION

Field of the Invention

The present invention relates to the art of measuring the retroreflectance properties of coatings and material surfaces and, more particularly, to an instrument having the capability of measuring retroreflectance to within a zero angle of incidence.

SUMMARY OF THE INVENTION

It is frequently necessary to measure the retroreflectance properties of materials when illuminated by electromagnetic radiation. Retroreflectance is defined as the ability of a surface to send reflected radiation back along the exact same path as the incident radiation. In the optical range of the electromagnetic spectrum, the retroreflectance properties of photometric standards as well as those of coatings and surfaces are of considerable interest from both a theoretical and a practical standpoint. More specifically, the opposition effect, which is the sharp nonlinear upsurge in brightness near the retroreflection direction, has application in the analysis of surface roughness and in remote sensing. The glory appearing around the shadow of an airplane on a cloud, when viewed in the retroreflecting direction (i.e., from the airplane), is an example of the peak in reflectivity occurring from the opposition effect. Similar halos have been observed, varying in intensity and size, above forests, grass, or cornfields. The development of a system in the prior art that permitted photometric observations to within one degree of the incident direction has shown the peaking of the opposition effect. Smoked MgO and $MgCO_3$ (photometric standards), $Al_2O_3$, various rocks, and other substances have been shown to peak. In fact, all the materials that have been measured have shown an opposition effect. The opposition effect has been quantified in various ways as by defining various opposition effect ratios such as the ratio of the retroreflection to that at a larger angle or a ratio of the retroreflection to the slope of the photometric curve projected to 0° angle; however, we have found it convenient to define the opposition effect as the ratio of the retroreflection (at 0°) to the reflection at 30° scattering angle.

When attempts have been made in the prior art to measure retroreflection, conventional goniometric reflectance measurement techniques have generally been employed. Briefly the conventional reflection goniometer comprises a radiation source, radiation chopper, optics, interference filters, and the like, with collimated radiation striking the test sample or specimen either at normal incidence or in a specular reflection geometry. The scattered radiation within a 1° acceptance angle is sensed by a photomultiplier following a monochromator. The range of measurement angles for reflectance ranges from 30° to 90°.

The conventional techniques of the prior art for opposition effect measurement at exactly 0° incidence in the presence of reflected radiation has not permitted measurement of retroreflection without artifacts of the techniques being introduced that degraded the results. The cube biprism arrangement of the subject invention overcomes the limitation of the prior art techniques and permits measurement of retroreflection from materials to be made with a high grade of accuracy. In the instrument of our invention, collimated radiation from a source is directed at the test specimen after first being passed through a biprism having a 45° diagonal semireflector surface in the path of the radiation. Radiation striking the target is reflected back on itself into the cube from whence it is reflected by the diagonal surface to the sensing system. A chopper interposed in the path of the radiation between the biprism and the specimen interrupts the radiation at a predetermined rate that is coordinated with the sensing system. In addition to serving the usual chopping function, the blade of the chopper acts as a reflecting surface that is used for reference purposes in a manner such as to eliminate the spurious responses that have plagued the attempts of the prior art to measure retroreflectance.

OBJECTS OF THE INVENTION

A principal object of the invention, therefore, is to provide an inexpensive uncomplicated means for making measurements of the retroreflectance properties of materials at incidence angles up to and including 0° incidence.

It is a further object of the invention to provide means employing a cube biprism, a chopper, and a sensing system, to measure the retroreflection properties of materials in which the radiation used in making the measurement is interrupted by the chopper at a rate synchronized with the sensing system and in which, moreover, the chopper is interposed in the path of the radiation between the biprism and the test specimen such that a technique is provided that substantially eliminates spurious responses.

It is another object of the invention to provide a device capable of measuring retroreflectance to zero degrees incidence which incorporates a uniquely positioned radiation chopper that serves as an efficient background discriminator of simplified and inexpensive construction.

DESCRIPTION OF THE PRIOR ART

The prior art shows examples of elements of the subject invention and also discloses the use of those elements in various optical systems. Thus, an optical device for surface characterization wherein a beam splitter is used to reflect light to a photometer which is first reflected from a rotating sample along the line of incident light is disclosed by P. Nisenson et al. (U.S. Pat. No. 3,782,827). Light choppers having various characteristics are also shown to be old in the art representatively by C. Ravitsky et al., H. L. Sachs, and K. Colbow et al. (U.S. Pat. Nos. 3,366,795; 3,398,285; and 3,435,213, respectively). However, although the prior art discloses apparatus useful in determining various electromagnetic characteristics of objects, it obviously is not addressed to providing a solution to the problems involved in measuring retroreflectivity at angles including zero-degrees incidence. Not only does the prior art appear not to disclose an instrument having the capability of measuring retroreflectivity at zero-degrees incidence, but it also does not disclose any examples of apparatus using a chopper for background discrimination in which the chopper is interposed in the path of the radiation between the beam splitter of the instrument and the target specimen.

DESCRIPTION OF THE DRAWINGS

For the purpose of illustrating the invention, there is shown in the drawings the forms which are presently preferred; it should be understood, however, that the invention is not necessarily limited to the precise arrangements and instrumentalities here shown.

DESCRIPTION OF THE PREFERRED EMBODIMENTS

Figure 1:
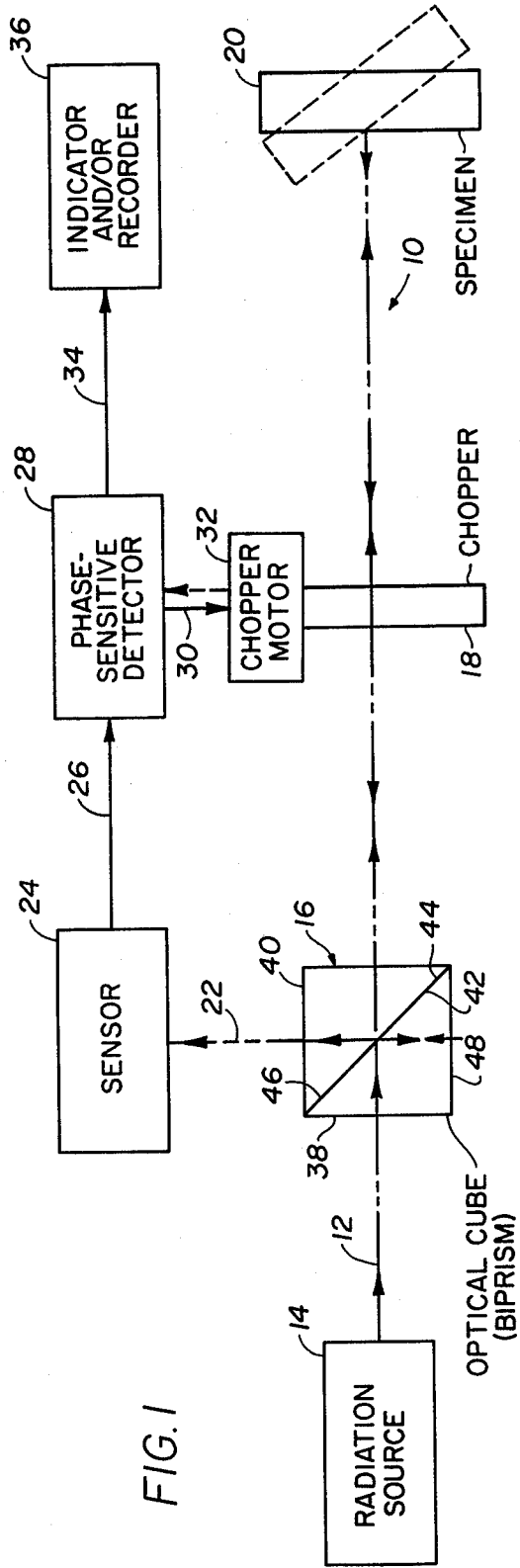
FIG. 1 is a schematic diagram of an embodiment of the retroreflectance measuring means of the invention.

Referring now to the drawings, FIG. 1 illustrates in diagrammatic form the instrument 10 of the invention. In this arrangement, a beam 12 of collimated radiation from a source 14 is directed through an optical cube biprism 16 and a radiation chopper 18 to the test sample or specimen 20. Associated with biprism 16 in the path 22 of reflected radiation therefrom is a radiation sensor 24 which serves to transduce the radiation incident upon it and produce an electrical signal output proportional to the incident radiation. This output signal is supplied through line 26 to a phase sensitive detector 28 whose internal reference generator signal is supplied through line 30 to synchronize the drive motor 32 of chopper 18. The output of the detector is supplied through line 34 to means such as indicator and/or recorder 36 by which the results of the measurements made by the apparatus are made available in a form suitable for utilization. In an alternate configuration, the chopper or drive motor may replace the internal generator as a source of primary phase reference to the phase sensitive detector 28.

Figure 2:
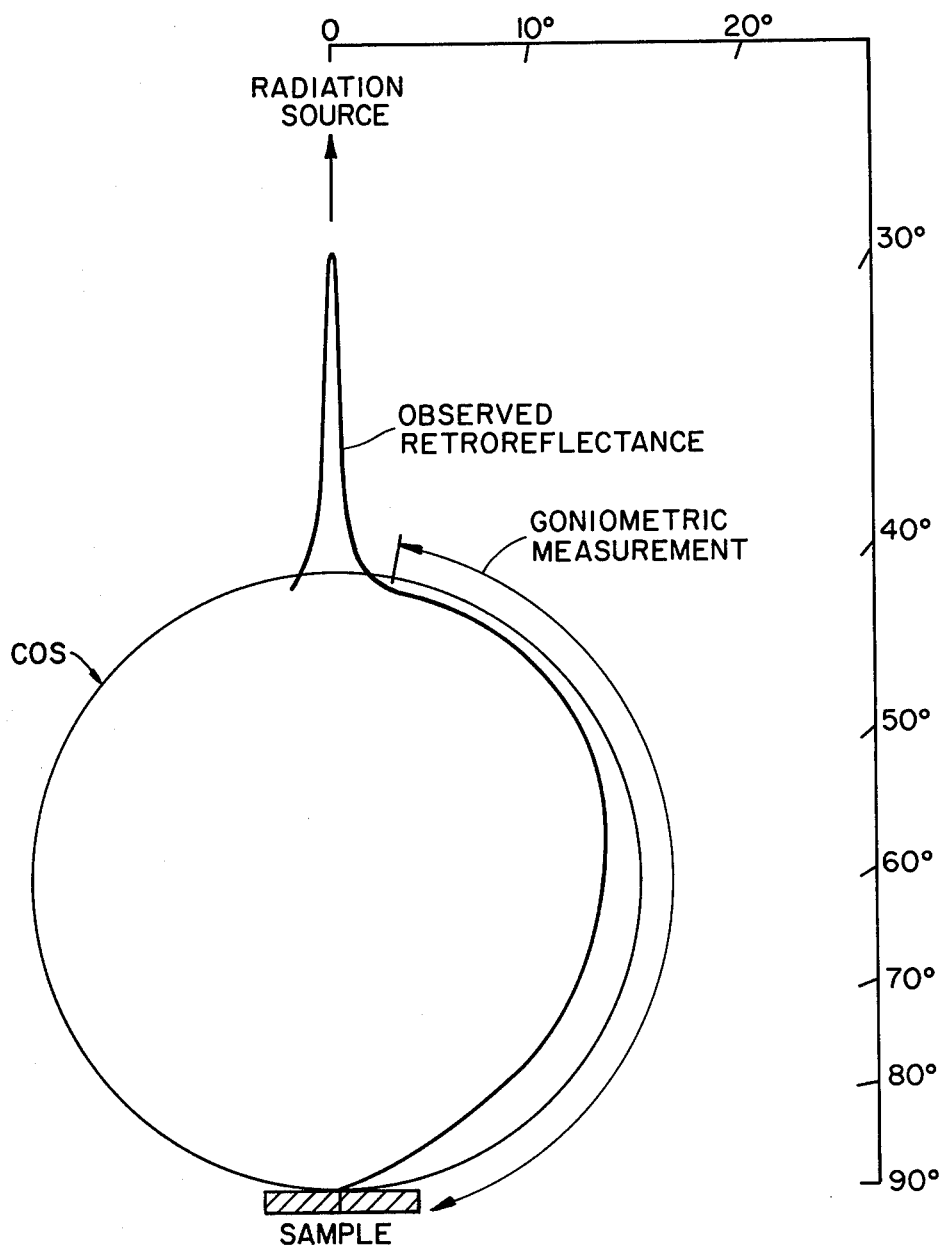
FIG. 2 is a polar diagram of the reflectance properties of the surface of a specimen.

The radiation used to measure the retroreflectance properties of a surface can be selected from any suitable frequency or frequency band of the electromagnetic spectrum. We have used low coherence (incandescent) illumination to make observations between 0.6 and 1.105μm and have used coherent laser illumination at 0.6328μm. An example of a retroreflectance measurement made with the incident beam perpendicular to the specimen surface by the instrument of the invention for BaSO$_4$ at 0.600μm wavelength is shown at FIG. 2. In FIG. 2 the brightness of the surface versus scattering angle is plotted on a polar diagram. It will be recognized that the "optics" of the apparatus will be, as is well known in the art, governed by the radiation wavelength employed and will generally be fused quartz for the visible range and near-ultraviolet and KRS-5 for the infrared. If frequencies in other bands of the electromagnetic spectrum, such as microwaves, are used the "optics" will be selected accordingly in a well-known manner.

In this apparatus, an optical cube or biprism 16 or a suitable equivalent is used as a beam splitter. Biprism 16, as is known, can comprise two short rectangular glass prisms 38 and 40 whose diagonal faces 42 and 44, respectively, are coated with semi-reflecting materials, or they may be cemented together with a material of refractive index different from the prisms to form a cube in which the joined faces form a 45° diagonal semi-reflecting surface 46.

Radiation chopping in accordance with the technique of this invention is by means of chopper 18 driven by a variable-speed motor 32 whose speed is controlled in a well-known manner by the reference source of the phase sensitive detector 28 or the control function may be accomplished with the motor as the primary phase reference. An arrangement suitable for the purpose can employ, for example, either a Model 222 or a Model 192 variable-speed light chopper (commercially available from Princeton Applied Research Corporation, Princeton, New Jersey) having its chopping speed synchronized at a desired speed such as, for example, 91Hz by signals from a phase sensitive detector, such as the Model HR-8 precision lock-in amplifier which is commercially available from the same company. Any suitable sensor 24 such as an RCA 1P28 photomultiplier or a solid state detector used, for example, in a Model 13U spectrometer monochromator (commercially available from the Perkin-Elmer Corporation, Norwalk, Conn.) can be used to supply the signal input to the phase sensitive detector 28. Indicator and/or recorder 36 can be any suitable means for measuring or displaying the signal output from the detector 28 and can comprise an oscilloscope and/or a chart recorder. A recorder suitable for use is a Speedomax Type G strip chart recorder available from Leeds & Northrop Co., North Wales, Pa.

In a measurement operation, the target specimen 20 is aligned at a zero-degree incidence in the path of irradiance from radiation source 14 (it will be appreciated that other angles up to ±90° may be used as desired and the mounting means (not shown) can be provided with suitable means to effect the necessary adjustments). Collimated radiation 12 from the source passes into the cube biprism 16 and a part of the radiation goes directly through and is incident on the specimen. Retroreflected radiation from the specimen returns back into the biprism along the original path and is reflected off the semi-reflecting diagonal surface 46 from whence it passes out of the biprism and is incident on sensor 24. A further part of radiation 12 from the source enters the biprism and is reflected off diagonal surface 46 such that it is incident on the bottom surface 48 (some radiation passes through to objects in the area surrounding the system) from whence part of it is reflected back along its original path and through the diagonal surface such that it also is passed to the sensor 24. It will be seen that under these conditions the sensor is exposed to retroreflected radiation from the specimen, internal reflections from the biprism, and also stray background scattered radiation. Periodically, however, the radiation passing directly between the biprism and the specimen is interrupted by the blade of the chopper 18; under this circumstance, retroreflected radiation from the specimen will be cut off and the sensor will be exposed only to reflections from the chopper blade, internal reflections from the biprism, and to the stray background radiation. Thus, the sensor will supply to the phase-sensitive detector 28 output signals representative both of the condition in which the reflected radiation incident on the sensor includes a component representing retroreflectance from the specimen and of the condition in which the sensor input does not include a radiation component from the specimen. The output signals from the sensor are processed in the detector which, in a manner well known in the art, supplies to the chopper motor 32 a chopper speed and phase synchronizing signal and supplies also an output voltage to the indicator and/or recording means 36 consisting only of the dc component of the chopped phase rectified output signal. The chopped signal will be understood to mean the maximum signal minus the signal components not resulting from the retroreflectance from the test specimen. Means 36 will process the signal output from the detector to present the information contained therein in a suitable desired form for utilization by the operator.

In this invention, the blade of the chopper provides a constant reference reflecting surface. It will be appreciated that, since the chopper blade has a measurable retroreflectance, it is necessary to establish an absolute or near absolute zero. This absolute reference can be obtained by positioning a light trap in the beam ordinarily striking the specimen. With the equipment described herein, the signal from the light trap has been determined to be less than 1%. This was comparable to read-out accuracy. The light trap (and the chopper blade) had retroreflecting properties that resulted in a dynamic range of $10^6$ (i.e., the reflectances relative to the light trap can be measured from 100% down to 0.01% to better than two significant figures, although the absolute zero point of the light trap was only calibrated to within 0.1%).

Figure 3:
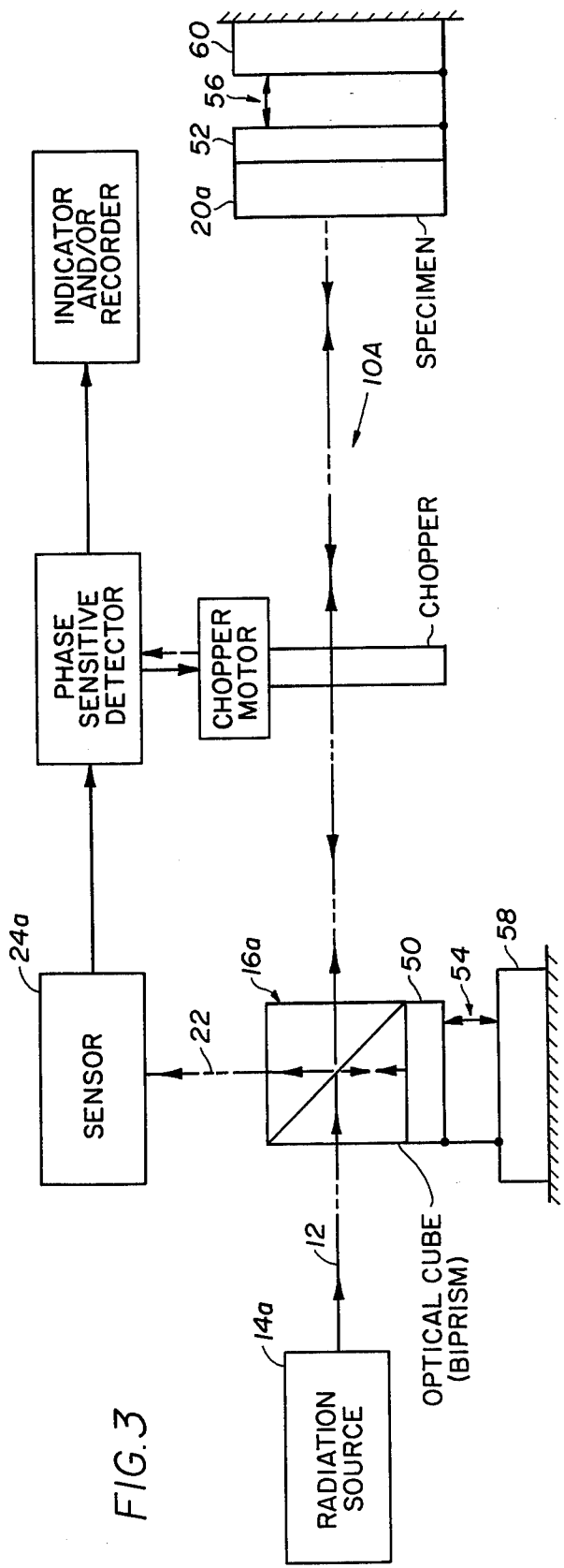
FIG. 3 is a schematic diagram of an alternate embodiment of the retroreflectance measuring means of the invention.

The arrangement illustrated in FIG. 1 with the chopper positioned as shown permits the use of a cube biprism as a beam splitter with exactly normal incidence of radiation upon the test specimen. To permit measurements that will give the slope of the opposition effect peak, the mounting means of the biprism and the specimen can be made adjustable such that deviations are provided in the paths of the radiation used to make the analyses. Conventional goniometric means are used to obtain reflectances at angles, for instance, at 30° to 90°. As shown in the retroreflectance measuring apparatus 10A embodied in FIG. 3, the mounting 50 of biprism 16a and the adjustable mounting 52 of the specimen 20a are connected by appropriate linkages 54 and 56 to suitable three-angle adjustment means 58 and 60 respectively, with means 58 also providing the required three-coordinate linear motion. Using this arrangement, the biprism and/or specimen can be adjusted such that reflected radiation may be sensed by sensor 24 a desired number of degrees off the incident direction. For example, should a measurement with an included (phase) angle of 1½° off the incident direction be desired, a mirror substituted for the specimen would be rotated ¾° and the biprism would be rotated empirically (the adjustment will be dependent on the index of refraction of the biprism) until a maximum sensed signal will indicate the required included angle is obtained. Then the specimen is substituted for the mirror and the desired measurement is made. As will be apparent, the size of the apertures of the radiation source 14a and of the sensor 24a will govern the angular range of the adjustment that is feasible.

Although shown and described in what is believed to be the most practical and preferred embodiments, it is apparent that departure from the specific method and apparatus described will suggest themselves to those skilled in the art and may be made without departing from the spirit and scope of the invention. We, therefore, do not wish to restrict ourselves to the particular instrumentalities illustrated and described, but desire to avail ourselves of all modifications that may fall within the scope of the appended claims.

Having thus described our invention, what we claim is:

1. Apparatus for measuring the electromagnetic reflectance and retroreflectance properties of the surface of a body or test specimen comprising:

a radiation source for generating a collimated beam of electromagnetic radiation which is directed such as to be incident on said specimen;

beam splitting means interposed in the path of said beam for transmitting components of said beam and reflecting other components thereof, including radiation reflected from said specimen, and stray ambient radiation;

radiation sensor means exposed to radiation reflected substantially by said beam splitter and producing an output signal in response to said reflected radiation;

radiation chopping means interposed in the path of said beam intermediate said beam splitter and said specimen for periodically blocking said radiation directed at said specimen whereby, when said chopper blocks reflectance from said specimen, the radiation reflected by said beam splitter into said sensor serves as a reference signal and, when the chopper passes radiation, the reflected radiation incident on said sensor serves as a measuring signal for determining reflectance from said specimen;

sequencing means for regulating the chopping rate of said chopper;

detector means for receiving said sensor output signal and having means for processing said sensor signal in coordination with said sequencing means, said detector having further means for comparing said reference signal component and said measuring signal component and producing a difference signal therefrom that characterizes the reflectance of said specimen; and signal intelligence means receiving said difference signal and reducing said signal to a form suitable for utilization.

* * * * *